United States Patent
Phanstiel et al.

(10) Patent No.: US 9,212,131 B2
(45) Date of Patent: Dec. 15, 2015

(54) POLYAMINE TRANSPORT INHIBITORS AS NOVEL THERAPEUTICS

(75) Inventors: Otto Phanstiel, Oviedo, FL (US); Jennifer J. Archer, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 811 days.

(21) Appl. No.: 13/379,191

(22) PCT Filed: Jun. 21, 2010

(86) PCT No.: PCT/US2010/039334
§ 371 (c)(1),
(2), (4) Date: Mar. 19, 2012

(87) PCT Pub. No.: WO2010/148390
PCT Pub. Date: Dec. 23, 2010

(65) Prior Publication Data
US 2012/0172449 A1 Jul. 5, 2012

Related U.S. Application Data

(60) Provisional application No. 61/218,470, filed on Jun. 19, 2009, provisional application No. 61/252,423, filed on Oct. 16, 2009.

(51) Int. Cl.
| | |
|---|---|
| C07C 233/78 | (2006.01) |
| C07C 237/46 | (2006.01) |
| C07D 295/13 | (2006.01) |
| A61K 31/137 | (2006.01) |
| A61K 31/166 | (2006.01) |
| C07C 211/27 | (2006.01) |
| C07C 231/02 | (2006.01) |
| C07C 235/10 | (2006.01) |

(52) U.S. Cl.
CPC .............. *C07C 233/78* (2013.01); *A61K 31/137* (2013.01); *A61K 31/166* (2013.01); *C07C 211/27* (2013.01); *C07C 231/02* (2013.01); *C07C 235/10* (2013.01); *C07C 237/46* (2013.01); *C07D 295/13* (2013.01)

(58) Field of Classification Search
CPC ... C07C 237/46; C07D 295/03; A61K 31/135
USPC ........... 514/646, 647, 649, 655; 564/153, 367
See application file for complete search history.

(56) References Cited

FOREIGN PATENT DOCUMENTS

WO WO 2007071396 6/2007

OTHER PUBLICATIONS

Wang et al, J.Med.Chem., 2003, 46, 2672-2682.*
Kaur et al., A Comparison of Chloroambucil- and Xylene-Containing Polyamines Leads to Improved Ligands for Accessing the Polyamine Transport System, J. Med. Chem., 2008, vol. 51, pp. 1393-1401.
Wang et al., Defining the Molecular Requirements for the Selective Delivery of Polyamine Conjugates into Cells Containing Active Polyamine Transporters, J. Med. Chem, 2003, vol. 46, pp. 5129-5138.

* cited by examiner

*Primary Examiner* — Sudhakar Katakam
(74) *Attorney, Agent, or Firm* — Timothy H. Van Dyke; Beusse, Wolter, Sanks & Maire, PLLC

(57) ABSTRACT

Novel polyamine transport inhibitors have been synthesized and demonstrated to block the uptake of native polyamines into human cancer cells. A combination therapy of the transport inhibitor and DFMO (a drug which blocks polyamine biosynthesis) provided synergistic activity against a metastatic human colon cancer cell line. The strategy uses polyamine depletion and polyamine metabolism to generate reactive oxygen species within cells as a novel way to treat cancers. This approach may be implemented for widespread use in the treatment of diseases which rely upon polyamine transport activity for proliferation.

4 Claims, 7 Drawing Sheets

POLYAMINE TRANSPORT INHIBITORS AS NOVEL THERAPEUTICS

RELATED APPLICATIONS

This application claims priority to U.S. Ser. Nos. 61/218,470 filed Jun. 19, 2009, and 61/252,423 filed Oct. 16, 2009, which are incorporated herein in their entirety.

FIELD OF THE INVENTION

The present invention relates to compositions and methods for the treatment of disorders characterized by unrestrained cell proliferation and/or differentiation where control of polyamine transport is required, and more particularly to novel polyamine transport inhibitors, compositions, and methods for their use.

BACKGROUND

Polyamines are essential growth factors. As such, polyamine homeostasis is tightly regulated by synthetic and catabolic enzymes as well as transport systems. Certain cancers, like colorectal cancer, have a high need for intracellular polyamines and can be targeted via polyamine depletion strategies. Indeed, there are four major targets (polyamine synthesis, catabolism, import and export) which can initiate this outcome. Of these four, the synthetic and catabolic enzymes are well understood. However, the transport systems associated with polyamine import is a 'black box'.

Knowledge of the polyamine transport system is a critical gap in our knowledge base. Previous efforts to deplete cells of polyamines via specific inhibitors of polyamine synthesis do not block these cells from recovering via import of polyamines from the extracellular milieu. For example, treatment of HCT-116 colon cells with difluoromethylornithine (DFMO) inhibits ornithine decarboxylase (ODC) and limits putrescine production, i.e., one of the three native polyamines (Roy, U. K.; Rial, N. S.; Kachel, K. L.; Gerner, E. W. Activated K-RAS increases polyamine uptake in human colon cancer cells through modulation of caveolar endocytosis. Mol. Carcinog. 2008, 47, 538-553). However, this is merely a cytostatic effect as cells can continue to survive via their existing polyamine pools and import. Indeed, cell growth continues, when DFMO is removed.

While the genes associated with polyamine transport are known in E. coli, yeast and Leishmania, they are unknown in mammals. There are titillating reports by Belting and Gerner, which suggest that caveolin-dependent lipid rafts may be involved in mammals. E.g., (Roy, U.K.; Rial, N. S.; Kachel, K. L.; Gerner, E. W. Activated K-RAS increases polyamine uptake in human colon cancer cells through modulation of caveolar endocytosis. Mol Carcinog. 2008, 47, 538-553). The Gerner group has had some success treating colon cancers with DFMO (which blocks ODC and polyamine synthesis) in combination with non-steroidal anti-inflammatory drugs (NSAIDs), which facilitate polyamine export by an unknown process. The Belting group demonstrated polyamine uptake involves binding to proteoglycans. (refs: (a) Belting, M.; Mani, K.; Jönsson, M.; Cheng, F.; Sandgren, S.; Jonsson, S.; Ding, K.; Delcros, J.-G.; Fransson, L.-A. Glypican-1 Is a Vehicle for Polyamine Uptake in Mammalian cells: A Pivotal role for Nitrosothiol-derived nitric oxide. J. Biol. Chem. 2003, 278, No. 47, 47181-47189; b) Belting, M.; Persson, S.; Fransson, L.-A. Proteoglycan involvement in polyamine uptake. Biochem. J. 1999, 338, 317-323; c) Belting, M.; Borsig, L.; Fuster, M. M.; Brown, J. R.; Persson, L.; Fransson, L.-A.; Esko, J. D. Tumor attenuation by combined heparan sulfate and polyamine depletion. PNAS 2002, 99, No. 1, 371-376.)

The Porter group has also investigated the induction of spermidine/spermine acetyl transferase (SSAT), which tags polyamines for export via N-acetylation, as another approach to deplete cells of native polyamines (Porter C W, Ganis B, Libby P R, Bergeron R J. Correlations between polyamine analogue-induced increases in spermidine/spermine N1-acetyltransferase activity, polyamine pool depletion, and growth inhibition in human melanoma cell lines. Cancer Res. 1991 Jul. 15; 51(14):3715-3720). SSAT action increases the amount of exportable polyamines (N1-acetylpolyamines) available. Without knowledge of the polyamine transporter (PAT) and a technology to inhibit its uptake of extracellular polyamines, the above anti-cancer strategies will always have to contend with polyamine uptake. Uptake provides a rescue mechanism from intracellular polyamine depletion. There is an urgent need therefore to develop PAT inhibitors which block this 'rescue pathway' of polyamine import.

DETAILED DESCRIPTION

The inventors have synthesized a homologous series of anthracene-polyamine conjugates, which are the subject of previously filed patent applications as anti-cancer drugs that use the polyamine transporter (PAT) for cell entry. The inventors have continued their research in this area and have now designed dimeric analogues which append two polyamine chains to an anthracene core. These dimeric systems have revealed enhanced targeting of cells via their polyamine transporter (PAT). These agents may also block the action of the polyamine transporter. Furthermore, the inventors have designed trimeric systems which actually inhibit the transporter.

Accordingly, in certain embodiments, the invention is based on the discovery that specially-designed polyamine analogues can compete with naturally-occurring polyamines for cell-surface receptors. This action has tremendous therapeutic value to the medical community. For example, cancer cells require polyamines to grow and can either biosynthesize them or import them from the extracellular environment. Dosing of cells with drugs (DFMO, FIG. 1) which block the biosynthesis of polyamines (eg. DFMO blocks putrescine production, FIG. 1) leads to cell arrest and typically a cytostatic effect. Dosing cells with a polyamine transport inhibitor, like those disclosed herein, blocks the entry of extracellular polyamines. Combination therapies which dose cells with an inhibitor of polyamine biosynthesis (e.g., difluoromethylornithine, DFMO) and an inhibitor of polyamine transport (compounds 3-10) have tremendous value to medicine as they provide a novel approach to limit cell growth via polyamine depletion or polyamine starvation. Since polyamines are an absolute requirement for life, cancer cells will not grow without their required polyamine pools. As such this invention provides a key tool that has been missing in the medical arena, i.e., potent polyamine transport inhibitors. As such this invention provides novel polyamine transport inhibitors (PTI)s based on two new structural motifs. One series consists of a tetraamine linked to an anthracene via a methyl group and the other series consists of a three polyamines linked to a benzene ring via a methyl group in meta positioning, a benzene ring via N acylation, or alternatively a citric acid core.

Figure 5:
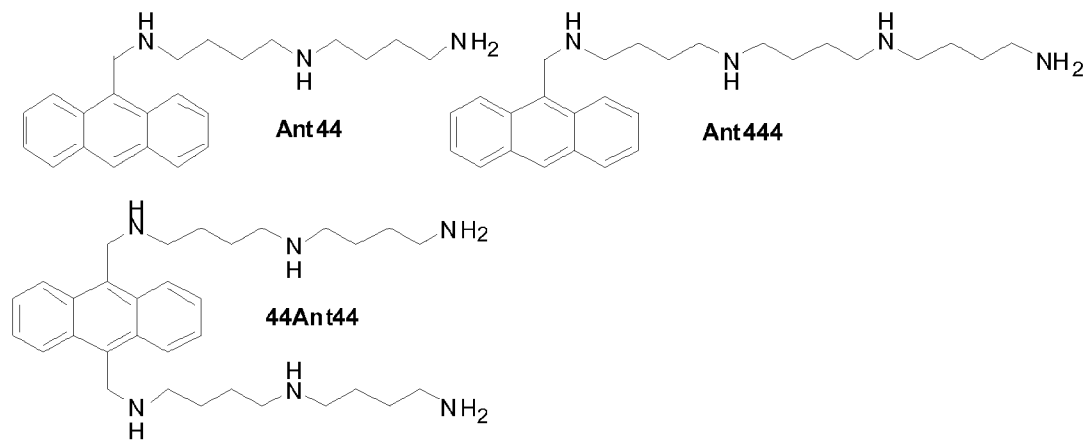
FIG. 5 relates to a diagram showing the structure of substituted Ant embodiments.

Anthracenyl tetraamines useful as a PTI in accordance with the teachings herein include those taught in U.S. Pat. No. 7,728,040, which is incorporated herein by reference. Moreover, FIG. 5 shows an example of a linear anthracenyl methyltetramine Ant-444, where the numbers refer to the number of carbons between each amine group. Other specific examples include Ant-544, Ant-443, Ant-354, Ant-543, Ant-343, Ant-344, Ant-334, and Ant-554.

The inventors demonstrate for the first time the efficacy of this combination approach (blockade of both polyamine transport and polyamine biosynthesis) as a new therapeutic approach to treat disorders, e.g., cancers, characterized by unrestrained cell proliferation and/or differentiation where control of polyamine transport is required. In particular, we show efficacy against CHO, SW620, L3.6pl, and MiaPaca-2 cell lines. Thus, our inhibitors are effective in treating both primary and metastatic colon and pancreatic cancer cells. [Note: CHO cells can be used as a model of a cell type with activated polyamine transport.] This is important because metastases are difficult to treat. The inventors also showed the SW480, RKO, HCT-116 and Panc-1 respond to DFMO in a time dependent matter and therefore it is concluded that they will also respond to DFMO+PTI therapy as the DFMO response is the limiting factor in this combination therapy. Also, the data demonstrates that this is a general phenomenon and various cell lines and tumor grades are susceptible to the therapeutic approaches disclosed herein.

Moreover, inhibitor embodiments are selective. For example, the 'triamide' inhibitor 5c and *triamide-444 (FIG. 4) selectively blocks import of putrescine and to a lesser extent the other native polyamines (spermidine and spermine see FIG. 1) at the dosage used. In this regard, the inventors have made putrescine-selective inhibitors, which is believed to be the first synthesis of such compounds.

The inventors have developed the total synthesis of new compositions of matter and demonstrate the efficacy of these polyamine analogues to block uptake of native polyamines into mammalian cells via two assays.

The first assay implements the growth of mammalian cells in a 96 well plate format on tissue culture plates.

1.) The media contains a maximum of 2 mM aminoguanidine and a minimum of 0.25 mM aminoguanidine to prevent a cell culture artifact (i.e., degradation of native polyamines and PTI structures that contain terminal amine structures (e.g., trimer 3c) by bovine serum amine oxidases present in the cell culture media). As a general rule, aminoguanidine (AG) is not dosed at a concentration which induces 20% or more cytostasis in the cell line examined. This minimizes AG side-effects. All of the following treatments are begun 24 hours after seeding the cells.

2.) DFMO is titrated in concentration and over time to determine the concentration and day that gives approximately 50% (±10%) reduction in growth compared to the control. Using 10 uM of a native polyamine (putrescine, spermidine, or spermine) should fully rescue cell growth of DFMO treated cells at this time and concentration compared to the control.

3.) The maximum tolerated dose (MTD) of the PTI is determined by titrating it without the presence of DFMO or polyamine. The MTD is defined as the maximum concentration of the drug (e.g., PTI) that is shown to keep 100% of the cell population alive compared to the control±10%.

4.) The minimum amount of the respective native polyamines (putrescine, spermidine, or spermine) that can rescue DFMO-treated cells is determined by titration at the time and concentration of DFMO that gives 50% (±10%) reduction in growth compared to the control as in step 2 above.

5.) The ability of DFMO to enhance toxicity of the PTI is determined by treating DFMO at the time and concentration of DFMO that gives 50% (±10%) reduction in growth compared to the control as in step 2 and treating the PTI at its MTD. If increased toxicity is observed compared to the DFMO only control (step 2), then the PTI needs to be re-titrated to find the dose in which the PTI does not show a difference in growth compared to the DFMO only control from step 2. This is defined as the "MTD under DFMO treatment."

6.) The combination of DFMO, polyamine, and PTI are treated concomitantly after 24 hours of growth in a 96-well tissue culture treated plate. The duration of treatment is determined by step 2 for all three reagents. The concentration of DFMO is determined in step 2, the concentration of polyamine is determined in step 4 and the concentration of PTI is determined by step 3, the MTD. Note if the MTD of the PTI is altered by the presence of DFMO then the "MTD under DFMO treatment" is used as determined in step 6. The untreated control cells, DFMO only treatment, and DFMO+ polyamine treatment, must be shown on the same plate as the experimental samples with PTI to ensure that these controls are working properly.

Figure 2:
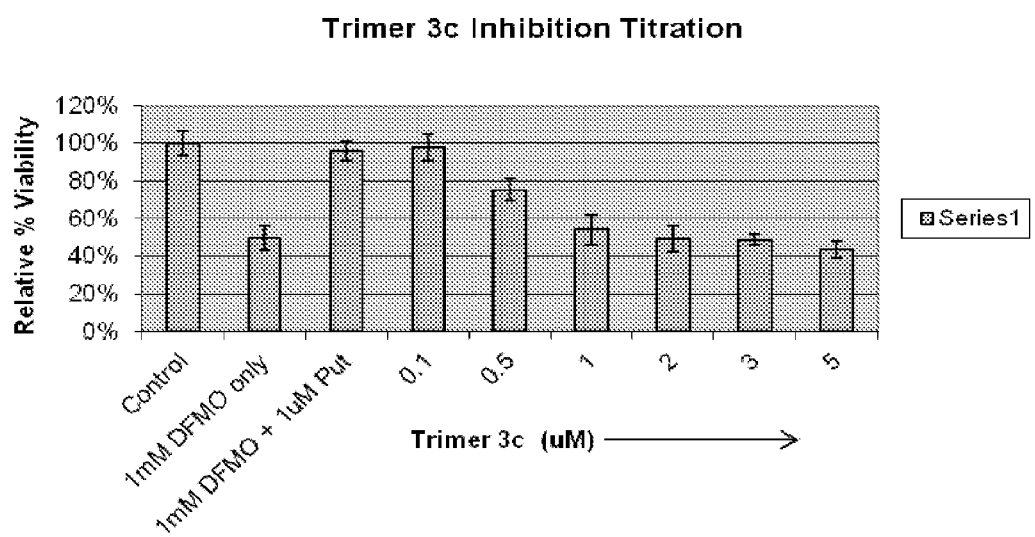

The first assay measures the ability of the new transport inhibitors to block rescue of DFMO-treated cells by putrescine (a native polyamine). As a control experiment we treated metastatic colon cancer cells (SW620) with DFMO (1 mM) and saw 50% reduction in growth as measured by the MTS assay (FIG. 2). In the presence of putrescine (1 uM) the DFMO-treated cells (1 mM) were 'rescued' and showed viability/growth equivalent to that of the control. However when putrescine (1 uM) is given concomitantly to cells treated with DFMO (1 mM) and the transport inhibitor (trimer 3c), the inhibitor blocks the ability of putrescine to rescue the growth reduction effects of DFMO, thus leading to polyamine starvation. We speculate that this 'block of rescue' occurs because the polyamine transport receptor is on the cell surface (putatively heparin sulfate and other sulfated carbohydrates) and the inhibitor blocks the native polyamine (putrescine) from entering the cell and cannot provide the growth rescue event as observed.

The second assay measures the ability of the new transport inhibitor (the trimer 3c) to block rescue of DFMO-treated cells by spermidine. The trimer 3c also showed efficacy in treating metastatic human pancreatic cancer cells (L3.6pl). As shown below, the L3.6pl cells were dosed with 5 mM DFMO, which reduced their viability during the 48 hour incubation period to 60% of the control growth without DFMO ($2^{nd}$ column). However, these cells were rescued by the addition of exogenous spermidine (0.5 □M, $3^{rd}$ column). This demonstrates that a DFMO therapy alone would not be the most effective approach as the pancreatic cells would simply import exogenous polyamines like spermidine to avoid the DFMO-mediated effect. However, in the presence of the trimer (i.e., the polyamine transport inhibitor 3c) we were able to block this rescue effect of spermidine (Spd) in a dose-dependent fashion (3c: 0.1 to 5 □M). For example, 3c at 2 □M in the presence of DFMO (5 mM)+spermidine (0.5 □M) gave 60% viability ($7^{th}$ column). Without the presence of the trimer, spermidine rescues the cells and one observes >90% viability ($3^{rd}$ column). The resulting data is in Table 1 and FIG. 3.

TABLE 1

| L3.6pl Trimer Inhibition vs Spermidine | | 48 hour | 500 cells/well | .25 mM AG | 5 mM DFMO | 0.5 uM PA | | | | |
|---|---|---|---|---|---|---|---|---|---|---|
| Day 0 | | | | | | | Average | STD | Error | Day 0 control-blank |
| Blank | | 0.131 | 0.13 | 0.128 | 0.12 | 0.122 | 0.122 | 0.1255 | 0.0047 | 4% | |
| Control | | 0.242 | 0.23 | 0.202 | 0.245 | 0.237 | 0.227 | 0.2305 | 0.0156 | 7% | 0.1050 |
| Spermidine [μM] | | | | | | | | | | | |
| Blank | | 0.13 | 0.128 | 0.127 | 0.123 | 0.121 | 0.119 | | | | |
| Control | | 1.171 | 1.269 | 1.207 | 1.201 | 1.092 | 1.111 | | | | |
| 5 mM DFMO only | | 0.847 | 0.751 | 0.799 | 0.714 | 0.809 | 0.794 | | | | |
| 5 mM DFMO + 0.5 uM Spd | | 0.849* | 1.122 | 1.127 | 1.076 | 0.996 | 1.107 | | | | |
| | 0.1 | 1.058 | 1.15 | 1.008 | 1.14 | 1.106 | 1.036 | | | | |
| | 0.5 | 0.968 | 1.048 | 1.085 | 1.106 | 1.127 | 1.059 | | | | |
| | 1 | 0.796 | 0.934 | 0.931 | 0.977 | 0.974 | 0.923 | | | | |
| | 2 | 0.765 | 0.811 | 0.807 | 0.739 | 0.839 | 0.803 | | | | |
| | 3 | 0.651 | 0.773 | 0.726 | 0.793 | 0.713 | 0.731 | | | | |
| | 5 | 0.625 | 0.658 | 0.707 | 0.622 | 0.682 | 0.648 | | | | |

TABLE 1-continued

| | | Average | Aver-blank | std | % Error | Minus Day 0 | % Viability |
|---|---|---|---|---|---|---|---|
| Blank | | 0.1247 | | 0.0043 | 3% | | |
| Control | | 1.1752 | 1.0505 | 0.0656 | 6% | 0.9455 | 100% |
| 5 mM DFMO only | | 0.7857 | 0.6610 | 0.0467 | 6% | 0.5560 | 59% |
| 5 mM DFMO + 0.5 uM Spd | | 1.0856 | 0.9609 | 0.0539 | 5% | 0.8559 | 91% |
| | 0.1 | 1.0830 | 0.9583 | 0.0578 | 5% | 0.8533 | 90% |
| | 0.5 | 1.0655 | 0.9408 | 0.0560 | 5% | 0.8358 | 88% |
| | 1 | 0.9225 | 0.7978 | 0.0661 | 7% | 0.6928 | 73% |
| | 2 | 0.7940 | 0.6693 | 0.0359 | 5% | 0.5643 | 60% |
| | 3 | 0.7312 | 0.6065 | 0.0497 | 7% | 0.5015 | 53% |
| | 5 | 0.6570 | 0.5323 | 0.0330 | 5% | 0.4273 | 45% |

Figure 6:
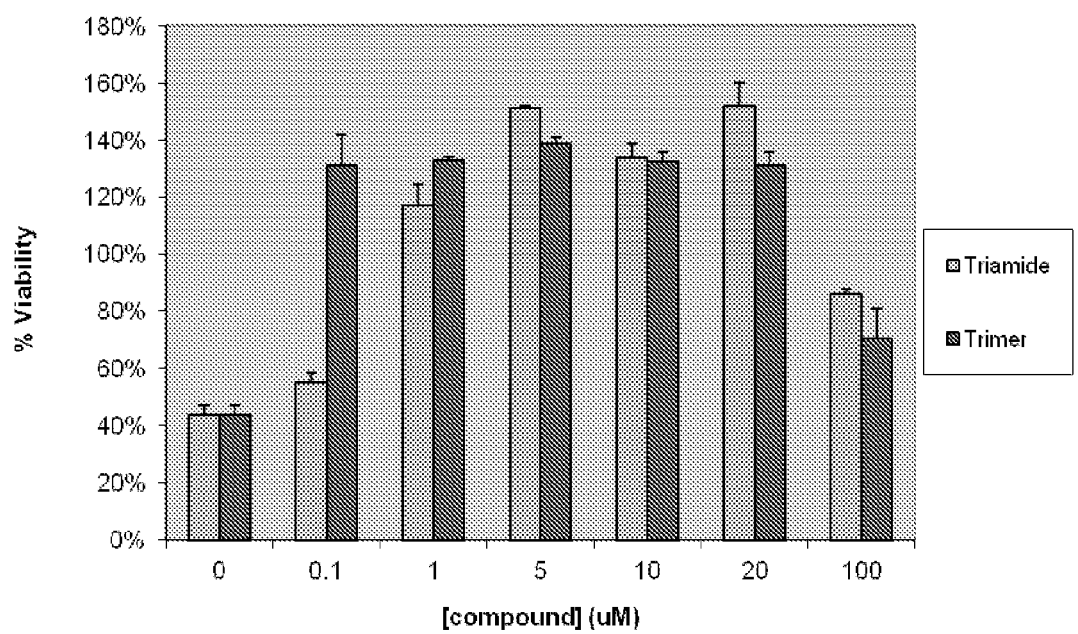
FIG. 6. In CHO-K1 cells, cytotoxic compound Ant44 was dosed at 0.5 μM in the presence of 2 mM aminoguanidine and either Triamide 5c or Trimer 3c at varying concentrations then incubated for 48 hours. Without either PAT inhibitor (5c or 3c) added, the Ant44 dosing of 0.5 uM resulted in 40% viability relative to untreated CHO-K1 cells. As the concentration of the PAT inhibitors were respectively increased (0.1 to 100 uM), they were able to block the Ant44 uptake into CHO cells. This resulted in higher % viabilities noted as the inhibitor dosage increased. In this sense the cells were rescued by the blockade of the polyamine transporter, which Ant44 has been shown to selectively use for cell entry. Note: dosing at 100 uM of either inhibitor in the presence of Ant44 (0.5 uM) caused moderate toxicity to these cells. In a direct comparison the trimer 3c was superior to triamide 5c in providing cell rescue. For example, 3c at 0.1 uM provided complete rescue from the Ant44 dose, whereas 5c when dosed at 0.1 uM was unable to rescue cells from Ant44. Note: 5c was able to rescue the CHO cells from Ant44 but required a higher dose of 5c (1 uM). Note: the triamide 5c was able to rescue the CHO cells from Ant44 but required a higher dose of 5c (1 uM). Note that all experiments performed contained a maximum of 2 mM aminoguanidine to prevent break-down of polyamine analogues in the serum. This cell culture artifact only arises due to bovine copper-dependent serum amine oxidases which are not present in humans and are therefore not of a concern. We also showed that Ant-tetraamines are also potent PAT inhibitors when dosed at low concentrations. This is reflective upon their low Ki values observed in L1210 cells (Phanstiel reference)
Figure 7:
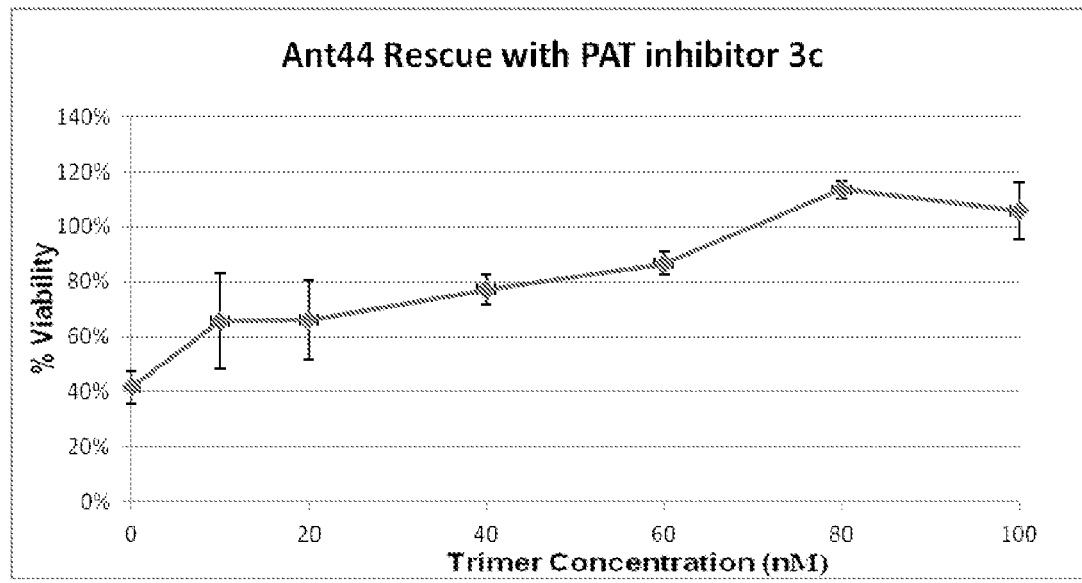
FIG. 7. In CHO-K1 cells, the PAT-selective cytotoxic agent Ant44 was dosed at 0.5 µM in the presence of Trimer 3c at varying concentrations (in nM) and incubated for 48 hours. Note that 2 mM aminoguanidine was added to the media to blockade degradation by serum amine oxidases. A further titration found that trimer 3c (80 nM) was able to protect CHO-K1 cells from Ant44 (0.5 uM).

The third assay measured the ability of a polyamine transport inhibitor (PTI) to bind to the polyamine transport receptor and competitively inhibit the cellular internalization of a cytotoxic polyamine transport active probe (PAT agonist) made by inventors (i.e., anthracen-9-ylmethyl-homospermidine conjugate, Ant44, see FIG. 5). In this manner, the PTI (e.g. 1 uM) dosed at completely non-toxic concentrations was able to block the uptake of the toxic Ant44 compound (Ant44 dosed at its $IC_{50}$ value, 0.5 uM). Indeed, both the new trimer and the triamide compound embodiments (structures in FIG. 4), were demonstrated to be potent PAT inhibitors and were effective in both assays. These experiments (FIGS. 6 and 7) were done in Chinese hamster ovary cells (CHO-K1) cells.

Figure 8:
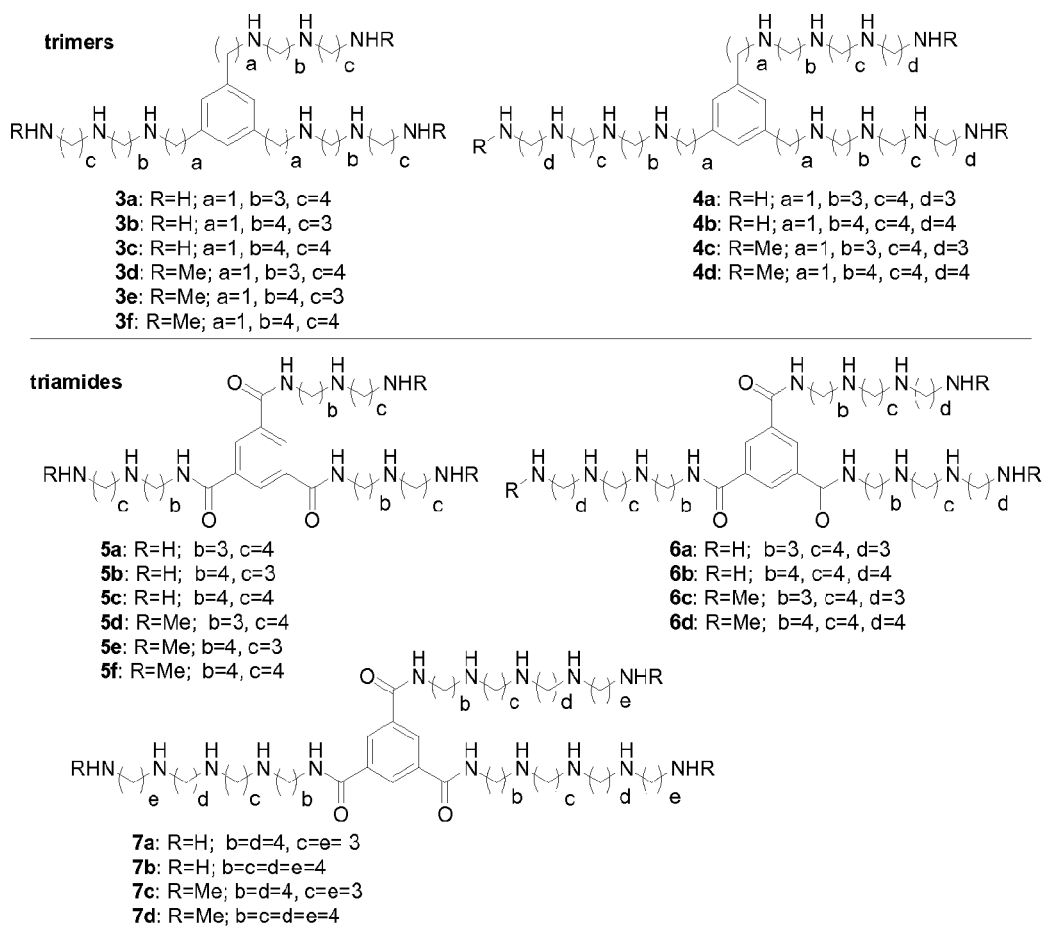
FIG. 8 Shows structures PAT inhibitor embodiments designated as 3-7
Figure 9:
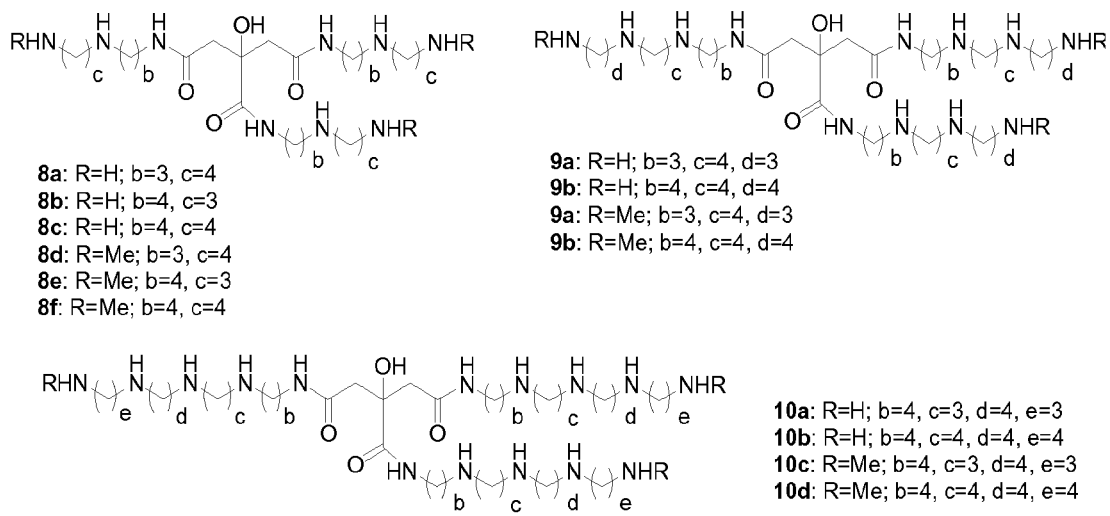
FIG. 9. shows structures of Citric acid Derivative embodiments designated as 8-10

The structures set forth in FIGS. 8 and 9 are trimeric scaffolds, which are also PAT inhibitors. The triamide agent 5c has been shown to be specific for putrescine. Trimeric structures with DFMO represent a novel colon cancer therapy. The three assays described above have demonstrated PAT inhibition for compounds 3c and 5c. Scheme 1 shows the synthetic approach used to make these materials.

Scheme 1. Modular synthesis of PAT inhibitors

Modular Synthesis

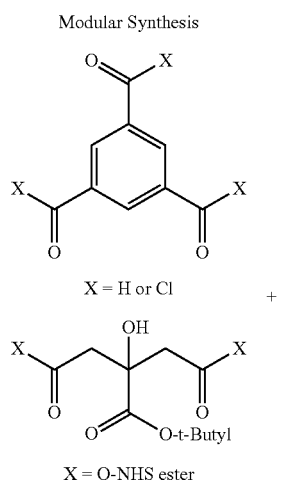

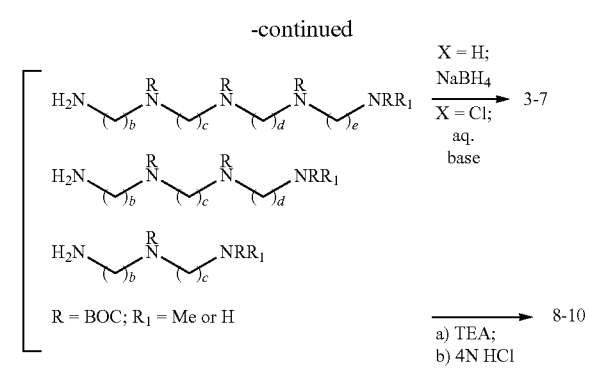

Armed with these new PAT-inhibitors, the inventors have demonstrated their efficacy in blocking polyamine entry to colon cancer cells. Blockade of polyamine growth factors into cancer cells is the basis of a therapeutic strategy. These experiments provide the basis for a new therapy for cancer, such as colon cancer.

As used herein, term "subject" is intended to include living organisms susceptible to conditions or diseases caused or contributed to by unrestrained cell proliferation and/or differentiation where control of polyamine transport is required. Examples of subjects include humans, dogs, cats, cows, goats, and mice. The term subject is further intended to include transgenic species.

As used herein, term "pharmaceutically acceptable salt" is intended to include art-recognized pharmaceutically acceptable salts. These non-toxic salts are usually hydrolyzed under physiological conditions, and include organic and inorganic bases Examples of salts include sodium, potassium, calcium, ammonium, copper, and aluminum as well as primary, secondary, and tertiary amines, basic ion exchange resins, purines, piperazine, and the like. The term is further intended to include esters of lower hydrocarbon groups, such as methyl, ethyl, and propyl.

As used herein, the term "pharmaceutical composition" comprises one or more of the PAT inhibitors described herein as active ingredient(s), or a pharmaceutically acceptable salt(s) thereof, and may also contain a pharmaceutically acceptable carrier and optionally other therapeutic ingredients. The compositions include compositions suitable for oral, rectal, ophthalmic, pulmonary, nasal, dermal, topical, parenteral (including subcutaneous, intramuscular and intravenous) or inhalation administration. The most suitable route in any particular case will depend on the nature and severity of the conditions being treated and the nature of the active ingredient(s). The compositions may be presented in unit dosage form and prepared by any of the methods well-known in the art of pharmacy. Dosage regimes may be adjusted for the purpose to improving the therapeutic response. For example, several divided dosages may be administered daily or the dose may be proportionally reduced over time. A person skilled in the art normally may determine the effective dosage amount and the appropriate regime.

As used herein, the term "effective amount" or "an amount effective" means an amount effective, at dosages and for periods of time necessary to achieve the desired result.

The compositions and methods described herein may be useful for the treatment and/or prevention of any disorder characterized by unrestrained cell proliferation and/or differentiation where control of polyamine transport is required. In one embodiment, the disorder is an inflammatory bowel disease, e.g., ulcerative colitis. In another embodiment, the disorder is cancer. In a particular embodiment, the cancer is one of colon cancer or pancreatic cancer.

Compound embodiments taught herein can be used in conjunction with other known therapeutic/cytotoxic agents. PCT application no. PCT/US10/35800 is referred to as a resource of such agents, and incorporated herein by reference. Moreover, this PCT application is cited to for a listing of cancers and cancer-related disorders that may be treated with the compounds and methods taught herein.

Figure 1:
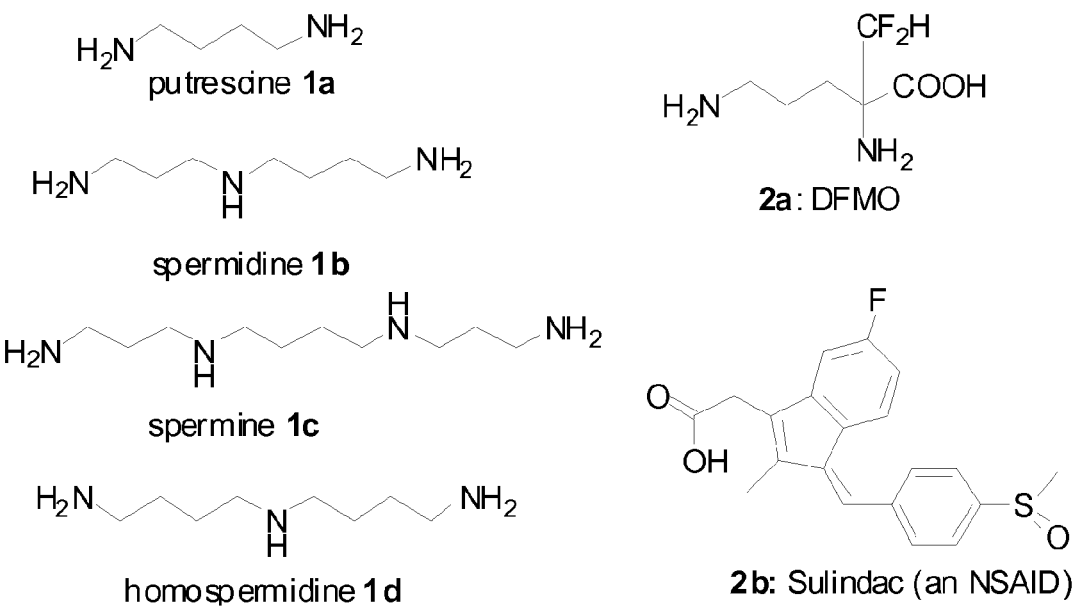
FIG. 1. The native polyamines (putrescine, spermidine and spermine), homospermidine, DFMO and sulindac FIG. 2. Relative viability of SW 620 cells after 72 hour incubation and demonstration of the combination therapy of DFMO (polyamine biosynthesis inhibitor) and PAT inhibitor 3c in the presence of putrescine (Put). DFMO (1 mM) only gave 50% viability; DFMO (1 mM) and Putrescine (1 uM) gave 100% viability or complete rescue; DFMO (1 mM), Putrescine (1 uM) and 0.1 uM of 3c gave 100% viability (unable to block Put intake), however DFMO (1 mM), Putrescine (1 uM) and 0.5 uM of 3c gave 75% viability (thru partial blockade of Putrescine uptake) and DFMO (1 mM), Putrescine (1 uM) and 1 uM (and higher) of 3c gave 50% viability (due to complete blockade of putrescine).

In one embodiment, the present invention provides for combination therapies, which include the following agents: polyamine biosynthesis inhibitor (DFMO, FIG. 1), a PAT inhibitor as described herein, and a drug that facilitates polyamine export (e.g., NSAID, sulindac, FIG. 1). Other NSAIDs that may be used include but are not limited to, aspirin, voltaren, naproxen, vioxx, ibuprofen, and tylenol.

In another embodiment, the invention pertains to a combination therapy of DFMO and a PAT inhibitor as described herein for use in treating disorders characterized by unrestrained cell proliferation and/or differentiation where control of polyamine transport is required. In one embodiment, the disorder is a cancer and in a particular embodiment is one of colon cancer or pancreatic cancer. The inventors have demonstrated this approach in cell culture with human colon and pancreatic cancer cell lines. Simply put, the combination therapy blocks polyamine biosynthesis and polyamine import via PAT. The combination of which should provide antitumor activity. The present inventors anticipate that this approach will be initially cytostatic, but may, given longer periods of time, be a cytotoxic event for the cancer cells.

In another embodiment, the invention pertains to the combination therapy of DFMO, a PAT inhibitor as described herein, and an NSAID for use in treating disorders characterized by unrestrained cell proliferation and/or differentiation where control of polyamine transport is required. In one embodiment, the disorder is a cancer and in a particular embodiment is one of colon cancer or pancreatic cancer. By this technology, DFMO should block polyamine synthesis, while PTIs will block polyamine import and the NSAID (i.e. sulindac) will facilitate the acetylation and export of intracellular polyamines. All three mechanisms working simultaneously should deplete cancer cells of their polyamines which should inhibit their growth and potentially induce cell death.

According to another embodiment, any chemotherapeutic which inhibits polyamine biosynthesis or depletes cells of polyamines (e.g., 5-fluorouracil, 5-FU) could also be used in combination with our PAT inhibitors to augment their potency. In this manner, the current invention of PAT inhibitors could increase the potency of existing chemotherapeutic agents like 5-FU. See PCT application no. PCT/US10/35800 for a listing of these and other therapeutic agents that my be used in conjunction with the PAT inhibitors taught herein.

Note: Gerner et al have already demonstrated the use of DFMO and Sulindac as a preventative therapy against colon cancer in a clinical trial. (a) Meyskens, Jr., F. L.; Gerner, E. W. Development of Difluoromethylornithine (DFMO) as a Chemoprevention Agent. *Clinical Cancer Research*, 1999, 5, 945-951.; b) Combination Chemoprevention for Colon Cancer Targeting Polyamine Synthesis and Inflammation, Eugene W. Gerner and Frank L. Meyskens, Jr. *Clinical Cancer Research* 2009, 15, 758-761.; c) and showed the uptake of polyamines via a caveolin dependent process in Roy, U. K.; Rial, N. S.; Kachel, K. L.; Gerner, E. W. Activated K-RAS increases polyamine uptake in human colon cancer cells through modulation of caveolar endocytosis. *Mol. Carcinog.* 2008, 47, 538-553). They did not show efficacy against cancer cells as is first disclosed herein.

EXAMPLES

Synthesis Details for 5c and 3c

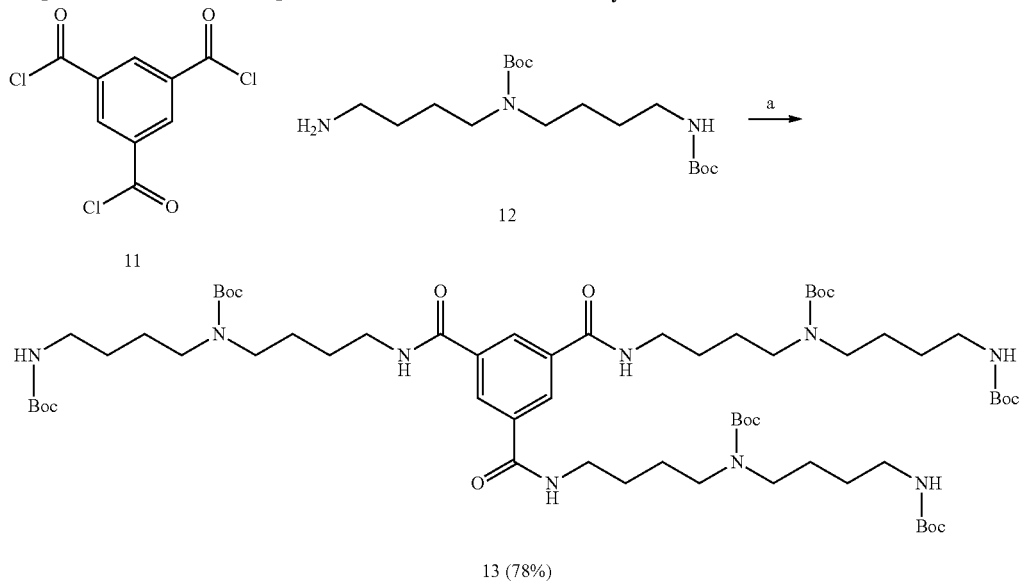

-continued
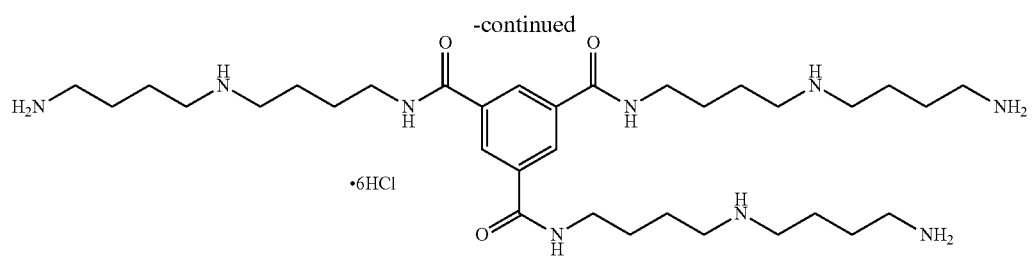
5c
Reagents: (a): CH$_2$Cl$_2$, H$_2$O, K$_2$CO$_3$, Aliquate, b) EtOH, 4N HCl

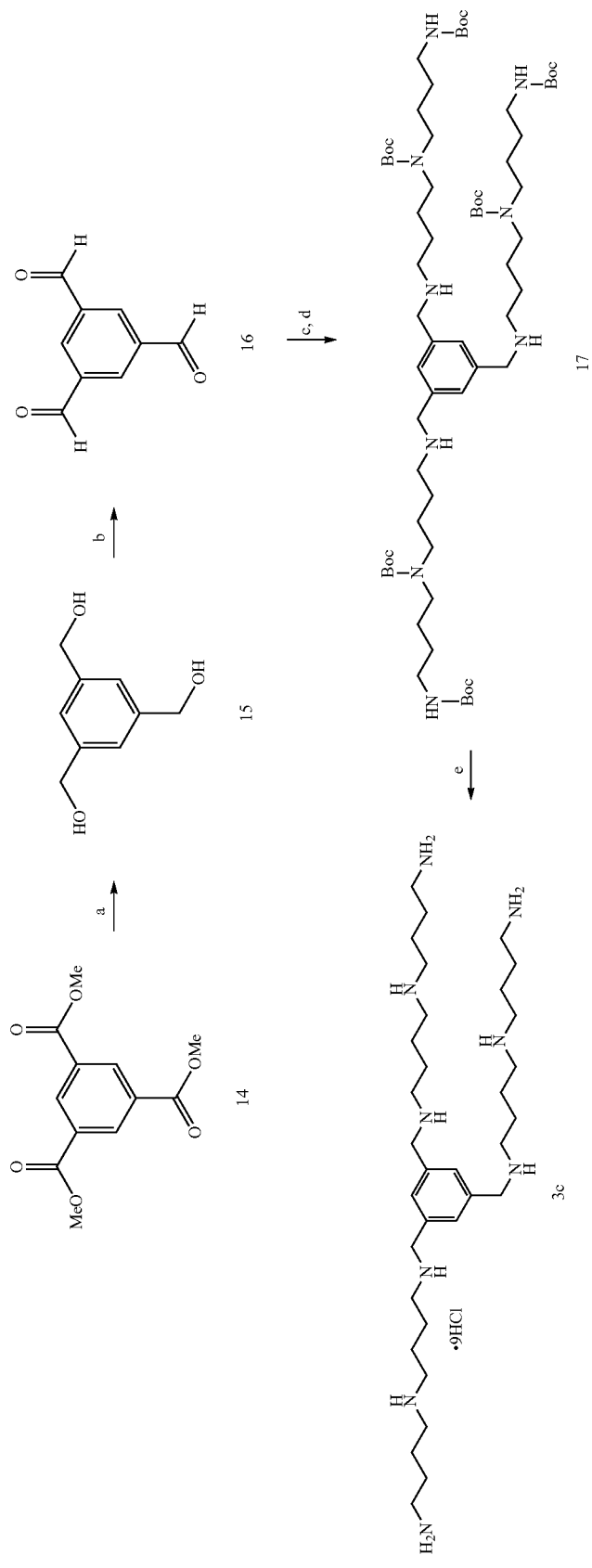

N-(4-Amino-butyl)-N'-(3,5-bis-{[4-(4-amino-butylamino)-butylamino]-methyl}-benzyl)-butane-1,4-diamine, Hydrochloride Salt, 3c A solution of triamine 17 (94 mg, 0.079 mmol) and ethanol (5 mL) was prepared and allowed to stir for 10 minutes at 0° C. A 4N HCl solution (10 mL) was added to the original solution dropwise and allowed to stir for 20 minutes at 0° C. and then at rt for 4 hours. TLC (92% $CH_2Cl_2$, 7% MeOH, 1% $NH_4OH$ $R_f$=0.40) was used to determine if the reaction was complete. After the reaction was complete, the solution was concentrated to give 3c (72 mg, 0.078 mmol, 99%). $^1H$ NMR ($D_2O$): δ 7.64 (s, 3H), 4.34 (s, 6H), 3.20 (t, 6H), 3.08 (m, 18H), 1.78 (m, 24H). $^{13}C$ NMR ($D_2O$): δ 135.8, 135.2, 53.3, 49.8, 49.8, 41.7, 26.8, 25.8, 25.73, 25.67.

Benzene-1,3,5-tricarboxylic acid tris-{[4-(4-amino-butylamino)-butyl]-amide}, Hydrochloride Salt, 5c A solution of triamide 13 (83 mg, 0.067 mmol) and ethanol (4 mL) was prepared and allowed to stir for 10 minutes at 0° C. A 4N HCl solution (8 mL) was added to the original solution dropwise and allowed to stir for 20 minutes at 0° C. and then at it for 4 hours. TLC (95% $CH_2Cl_2$, 4% MeOH, 1% $NH_4OH$ $R_f$=0.35) was used to determine if reaction was complete. After the reaction was complete, the solution was concentrated to give 5c (61 mg, 0.0663 mmol, 99%). $^1H$ NMR ($D_2O$): δ 8.32 (s, 3H), 3.47 (t, 6H), 3.10 (m, 18H), 1.83-1.74 (m, 24H). $^{13}C$ NMR ($D_2O$): δ 160.6, 154.0, 126.5, 120.4, 38.8, 38.4, 30.9, 30.4, 17.2, 15.5, 14.7, 14.5, 14.3. $C_{33}H_{63}N_9O_3 \cdot 6HCl \cdot 3.5H_2O$ theory C, 43.28; H, 8.37; N, 13.77. found C, 43.20; H, 8.26; N, 13.91.

[4-(3,5-Bis-{4-[tert-butoxycarbonyl-(4-tert-butoxycarbonylamino-butyl)-amino]-butylcarbamoyl}-benzoylamino)-butyl]-(4-tert-butoxycarbonylamino-butyl)-carbamic acid tert-butyl ester, 13

A solution of (4-Amino-butyl)-(4-tert-butoxycarbonylamino-butyl)-carbamic acid tert-butyl ester 12 (460 mg, 1.28 mmol) and $CH_2Cl_2$ (3 mL) was prepared. Note: 12 is a known compound (ref: "Total Synthesis of Petrobactin and Its Homologues as Potential Growth Stimuli for *Marinobacter hydrocarbonoclasticus*, an oil-degrading bacteria." Gardner, R. A.; Kinkade, R.[+]; Wang, C.; Phanstiel IV, O. *J. Org. Chem.* 2004, 69, 3530-3537). A solution of $K_2CO_3$ (420 mg, 3.04 mmol) and water (5 mL) was added to the original mixture. Aliquat (0.10 mL) was added and the mixture was cooled to 0° C. 1,3,5-benzenetricarboxylic acid chloride 11 (105 mg, 0.395 mmol) in $CH_2Cl_2$ (6 mL) was added dropwise to the original mixture and allowed to gradually warm and stir vigorously at rt for 6 hours. TLC (95% $CH_2Cl_2$, 4% MeOH, 1% $NH_4OH$ $R_f$=0.35) was used to monitor the reaction. After the reaction was complete, the aqueous layer was extracted three times in $CH_2Cl_2$ and saturated $Na_2CO_3$. The organic layers were combined and dried over anhydrous $Na_2SO_4$, filtered, and concentrated to give 590 mg of crude product. The crude was subjected to flash column chromatography (95% $CH_2Cl_2$, 4% MeOH, 1% $NH_4OH$ $R_f$=0.35) to give 13 (382 mg, 0.310 mmol, 78%). $^1H$ NMR ($CDCl_3$): δ 8.41 (s, 3H), 4.75 (br s, 3H), 3.49 (m, 6H), 3.23-3.06 (m, 18H), 2.78-1.30 (m, 78H).

1,3,5-Tris(hydroxymethyl)benzene, 15

Trimethyl-1,3,5-benzenetricarboxylate 14 (1.98 g, 7.83 mmol) in dry THF (30 mL) was added through a pressure-equalized addition funnel into a stirring suspension of $LiAlH_4$ (0.95 g, 24.9 mmol) in dry THF (65 mL) at 0° C. under an argon atmosphere. The mixture was allowed to warm to rt and stirred for 4 hours. $^1H$ NMR ($CDCl_3$) was used to monitor the reaction. After determining a large amount of starting material remained, additional $LiAlH_4$ (0.50 g, 13.1 mmol) was added to the reaction mixture and the reaction was allowed to proceed at RT for an additional 4 hours. $^1H$ NMR ($CDCl_3$) was used to determine if reaction was complete. After the reaction was complete, MeOH (25 mL) was used to quench the reaction. The suspension was filtered using Celite and the Celite was washed with MeOH (100 mL). The filtrate was concentrated under reduced pressure. The residue was stirred in THF (30 mL), $KHSO_4$ (3.53 g, 26 mmol) and Celite (1.53 g, 25.4 mmol) for 30 minutes. The suspension was filtered and washed with MeOH (50 mL). Solvents were removed under reduced pressure. The resulting solid was dissolved in hot ethyl acetate and filtered. The solid that remained at the filter was collected, dried and to yield triol 15 (0.954 g, 5.68 mmol, 73%). $^1H$ NMR (DMSO): δ 7.22 (s, 3H), 5.17 (br s, 3H), 4.48 (s, 6H).

1,3,5-Triformyl Benzene, 16

1,3,5-Tris(hydroxymethyl)benzene 15 (927 mg, 5.12 mmol) was suspended in $CH_2Cl_2$ (25 mL) and solid PCC (5.94 g, 27.6 mmol) was added. After 30 minutes of stirring, the reaction was diluted with acetone (10 mL) and was allowed to stir for 3 hr at RT. TLC (10% MeOH, 90% $CH_2Cl_2$ $R_f$=0.50) was used to determine if the reaction was complete. After the reaction was complete, the precipitated chromium salts were filtered off and washed with $CH_2Cl_2$. The aqueous layer was extracted 3 times in $CH_2Cl_2$ and saturated $Na_2CO_3$. The organic layers were combined and dried over anhydrous $Na_2SO_4$, filtered, and concentrated. Flash column chromatography (100% $CH_2Cl_2$ $R_f$=0.4) gave 16 (272 mg, 1.68 mmol, 33%). $^1H$ NMR ($CDCl_3$): δ 10.21 (s, 3H), 8.63 (s, 3H).

{4-[3,5-Bis-({4-[tert-butoxycarbonyl-(4-tert-butoxycarbonylamino-butyl)-amino]butylamino}-methyl)-benzylamino]-butyl}-(4-tert-butoxycarbonylamino-butyl)-carbamic acid tert-butyl ester, 17

1,3,5-Triformyl benzene 16 (32 mg, 0.197 mmol) was dissolved in 25% MeOH/$CH_2Cl_2$ (5 mL). A solution of Boc-protected homospermidine 12 (265 mg, 0.738 mmol) was added via an addition funnel. The reaction mixture was stirred overnight under a $N_2$ atmosphere. Loss of starting material was monitored via $^1H$ NMR and the disappearance of the aldehyde proton at 10.21 ppm. Upon conversion of the starting material, the solvent was removed in vacuo and the crude material was redissolved in a solution of 50% MeOH/$CH_2Cl_2$. To this new solution was added $NaBH_4$ (83 mg, 2.19 mmol) at 0° C. The solution was stirred overnight under a $N_2$ atmosphere. The solvents were removed under reduced pressure. The aqueous layer was extracted 3 times in $CH_2Cl_2$ and saturated $Na_2CO_3$. The organic layers were combined and dried over anhydrous $Na_2SO_4$, filtered, and concentrated. Crude material was dissolved in dry THF (10 mL) and allowed to stir for 20 minutes at 0° C. Solid 2-(tert-butoxycarbonyloyimino)-2-phenylacetonitrile (Boc-On, 51 mg, 0.206 mmol) was added to change the $R_f$ value of the starting diBoc amine and the solution was allowed to stir for 2 hours at 0° C. Upon completion the solvents were removed under reduced pressure. Residue was redissolved in $CH_2Cl_2$ and the aqueous layer was extracted 3 times in $CH_2Cl_2$ and saturated $Na_2CO_3$. The organic layers were separated, dried over anhydrous Na$_2$SO$_4$, filtered, and concentrated. Flash column chromatography (92% CH$_2$Cl$_2$, 7% MeOH, 1% NH$_4$OH R$_f$=0.40) afforded 17 (94 mg, 0.079 mmol, 40%). $^1$H NMR (CDCl$_3$): δ 7.16 (s, 3H), 4.72 (s, 3H), 3.78 (s, 6H), 3.18 (m, 18H), 2.64 (t, 6H), 1.69-1.19 (m, 78H).

Experimental Data for Compound 6b

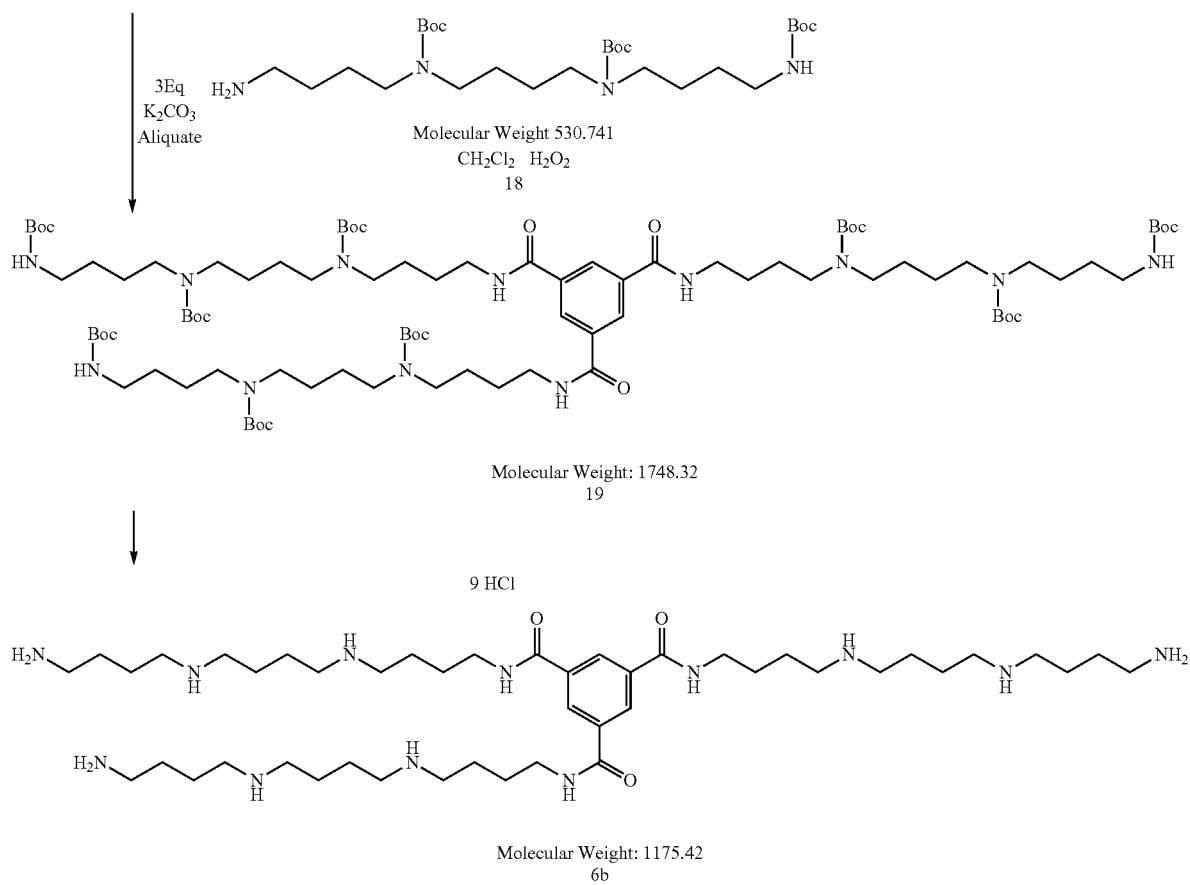

Synthesis of the Boc Protected Triamide 19

K$_2$CO$_3$ (1.0 g, 7.25 mmoles, 7.7 eq) was dissolved in H$_2$O (12 mL) and Aliquat (17 mg) and placed in a 100 mL flask. The tri-Boc tetraamine analogue 18 (1.68 g: 3.17 mmoles) was dissolved in CH$_2$Cl$_2$ (5 mL) was added to the flask. The mixture was cooled to 0° C. and the triacid chloride 11 (0.25 g: 0.9417 mmoles) was dissolved in CH$_2$Cl$_2$ (15 mL) and was slowly added dropwise to the flask while stirring. The reaction was warmed to room temperature and stirred for 6 hours. The product was extracted 3 times with CH$_2$Cl$_2$. The organic layers were separated, combined and dried over anhydrous sodium sulfate filtered and concentrated to give a viscous pale yellow oil. After high vacuum exposure, the product appeared as a flaky solid (1.33 g). The product was purified by column chromatography (5% MeOH in CH$_2$Cl$_2$) to yield 1.24 g (75% yield). Compound 19: $^1$H NMR (CDCl$_3$): δ 8.4 (s, 3H), 4.8 (br s, NH, 3H), 3.5 (br s, 6H), 3.2 (30H), 1.8-1.2 (m, 120H); $^{13}$C NMR (CDCl$_3$): δ 166.4, 156.2, 155.7, 135.4, 128.9, 79.5, 79.4, 79.1, 46.8, 45.8, 41.3, 41.1, 40.9, 40.3, 40.0, 39.8, 39.3, 29.58, 29.1, 29.1, 29.0, 28.6, 28.5, 28.47, 28.0, 27.9, 27.4, 27.1, 26.9, 26.5, 26.3, 26.1, 26.0, 25.6; elemental analysis C$_{90}$H$_{162}$N$_{12}$O$_{21}$ theory C, 61.83; H, 9.34; N, 9.61. found C, 61.64; H, 9.31; N, 9.38. Using TLC, only one spot was detected using the short wave UV, which was dark blue (R$_f$=0.26, 96% CH$_2$Cl$_2$, 4% MeOH)

Synthesis of triamide 6b. The BOC derivative compound 19 (1.37 g: 0.786 mmoles) and was dissolved in EtOH (52 mL) and cooled to 0° C. while stirring. 4N HCl (84 mL) was added dropwise. After the HCl was added, the reaction was allowed to warm to room temperature and stirred for 4 hours. The solvent was then removed under reduced pressure to give the product 6b HCl salt (781 mg, 84% yield). Compound 6b: $^1$H NMR (D$_2$O): δ 8.30 (s, 3H), 3.49 (t, 6H), 3.15 (m, 24H), 3.06 (t, 6H), 1.80 (m, 36H); $^{13}$C NMR (D$_2$O): δ 171.8, 137.82, 137.81, 131.9, 131.8, 50.6, 50.3, 49.93, 49.9, 49.8, 49.6, 49.55, 42.4, 42.1, 41.8, 41.5, 28.8, 28.6, 27.1, 26.9, 26.86, 26.76, 26.14, 26.0, 25.8, 25.78; elemental analysis C$_{45}$H$_{99}$Cl$_9$N$_{12}$O$_3$·6H$_2$O theory C, 42.11; H, 8.72; N, 13.10. found C, 12.94; H, 8.34; N, 12.94.

In one embodiment, the inventors sought to develop a novel drug class to be used in combination with DFMO for the treatment of colon cancer. Pursuant to this goal, the inventors sought to develop and identify novel PAT inhibitors which have toxicity profiles which are clinically acceptable and which induce polyamine depletion within cancer cells both in vitro and in vivo. Indeed, potent PAT inhibitors could be used in conjunction with DFMO (and possibly NSAIDs) as a multi-prong approach to effectively deplete intracellular polyamine pools and inhibit tumor growth.

The inventors hypothesized that multimeric polyamine platforms will inhibit the compensatory polyamine import processes present in human colon cancers and provide an effective anti-cancer therapy when used in conjunction with DFMO.

Early reports in the 1980s by the Porter group suggested that branched polyamines were effective substrates for PAT (e.g., N$^4$-benzylspermidine was shown to use PAT). (Porter C W, Cavanaugh P F, Ganis B, Kelly E, Bergeron R J (1985) Biological properties of N$^4$- and N$^1$,N$^8$-spermidine derivatives in cultured L1210 leukemia cells. Cancer Res. 45: 2050-2057.)

However, recent work has revealed that linear N1-substituted polyamines are superior ligands for PAT utilization. In terms of direct PAT inhibition, both the Poulin (BMCL, 1999, 9, 1709.) and the Graminski groups revealed that dimeric ligands could inhibit PAT in vitro (BMCL 2002, 12, 35-40.) and again found that linear substrates were better than branched polyamine "messages" in terms of interactions with the putative PAT. The number of charges was also found to play a role. Our own work demonstrated that the linear homospermidine (4,4-triamine, FIG. 1, 1d) message was superior in terms of targeting PAT. This information was gleaned from studying a homologous series of 'monomeric' anthryl-polyamine conjugates, wherein a specific polyamine message was appended to a fluorescent anthryl probe. This result was then expanded to include a bis-homospermidine dimeric compound (which had two homospermidine messages attached to the anthryl core) and was shown to be a hyper-efficient PAT ligand (A Comparison of Chloroambucil- and Xylene-containing polyamines leads to improved ligands for accessing the polyamine transporter. Navneet Kaur, Jean-Guy Delcros, and Otto Phanstiel IV. *J. Med. Chem.* 2008, 51, 1393-1401). Interestingly, a trimeric derivative containing three homospermidine messages was recently found to be a potent PAT inhibitor (A Comparison of Chloroambucil- and Xylene-containing polyamines leads to improved ligands for accessing the polyamine transporter. Navneet Kaur, Jean-Guy Delcros, and Otto Phanstiel IV. *J. Med. Chem.* 2008, 51, 1393-1401.). In this regard, the proposed work provides a new platform for PAT inhibitor design. In summary, the inventors have realized that one arm and two arm polyamine motifs are ligands for the polyamine transporter but three armed motifs are inhibitory. All three motifs must bind to the cell-surface recognition site (proteoglycans). The inventors have surmised that they can all compete with native polyamines for these receptors and could be deemed competitive inhibitors.

Lastly, the toxicity of polyamine drugs has long biased many against their develop as therapeutics. For example, polyamines are known to be potent inhibitors of NDMA receptors and ellicit potent CNS side-effects (Comparative Studies of Anthraquinone- and Anthracene-Tetraamines as Blockers of N-Methyl-D-aspartate Receptors. Jin, L.; Sugiyama, H.; Takigawa, M.; Katagiri, D.; Tomitori, H.; Nishimura, K.; Kaur, N.; Phanstiel, IV, O.; Kitajima, M.; Takayama, H.; Okawara, T.; Williams, K.; Kashiwagi, K.; Igarashi, K. *JPET* 2007, 320, 47-55.). Alkylated polyamines have failed in the clinic due to nephrotoxicity. Moreover, the free amine end group is a substrate for amine oxidases, which degrade the polyamine drugs in vivo. Any new proposal must take this into account in terms of drug design. There is a powerful bias in the community due to popularized failures. The inventors have addressed this aspect. First, they have found that N-methylated derivatives provide a way to avoid the amine oxidase degradation pathway (Designing the Polyamine Pharmacophore: Influence of N-substituents on the transport behavior of polyamine conjugates, Navneet Kaur[†], Jean-Guy Delcros[§], Jennifer Archer[†], Nathan Z. Weagraff[†], Bénédicte Martin[§] and Otto Phanstiel IV[†]* *J. Med. Chem.* 2008, 51, 2551-2560).

It is important to understand and be able to control all entry points which contribute to intracellular polyamine levels. According to our current knowledge, there are three methods by which cancer cells can avoid polyamine depletion and cell death. Never before has assessing how a complete inhibition of polyamine biosynthesis and polyamine import can work together with SSAT induction (which increases polyamine export) to deplete cells of polyamines been enabled. The compounds (3-9) provide the final tools needed to assess this strategy in humans. The inventors have designed experiments to block all possibilities and to see how and if cancer cells survive. This has lead to a multi-prong strategy which blocks PA synthesis via DFMO, and blocks import as well. Lastly, certain inhibitor embodiments contain a terminal aminopropyl group (e.g., 3b, 4a, 5a, 6a, and 7a) and they may also induce SSAT and export native polyamines as well.

Existing published data pertaining to this invention:

1) Burns lipospermine (a) Synthesis of Bis-Spermine Dimers that are potent Polyamine transport Inhibitors, Graminski, G. F. et al *Bioorganic & Medicinal Chemistry Letters* 2002, 12, 35-40;

b) Lipophilic Lysine-Spermine Conjugates are potent Polyamine transport inhibitors for use in combination with a polyamine biosynthesis inhibitor. Burns, M. R. *J. Med. Chem.* 2009, 52, 1983-1993.

The Burns group has made efficient PAT inhibitors. However, these are potential substrates for polyamine amine oxidases (PAO). As such, they did not safeguard against PAO activity as has been done here via the suggested N-methylation.

2) Phanstiel dimer paper A Comparison of Chloroambucil- and Xylene-containing polyamines leads to improved ligands for accessing the polyamine transporter. Navneet Kaur, Jean-Guy Delcros, and Otto Phanstiel IV. *J. Med. Chem.* 2008, 51, 1393-1401.

3) Phanstiel N-Me paper: Designing the Polyamine Pharmacophore: Influence of N-substituents on the transport behavior of polyamine conjugates, Navneet Kaur[†], Jean-Guy Delcros[§], Jennifer Archer[†], Nathan Z. Weagraff[†], Bénédicte Martin[§] and Otto Phanstiel IV[†]* *J. Med. Chem.* 2008, 51, 2551-2560. Here we demonstrate the N-methylation protection from drug degradation via PAO action by performing experiments in the presence and absence of aminoguanidine (a known amine oxidase inhibitor).

4) Poulin inhibitors (a) Xylated Dimers of putrescine and polyamines: Influence of the Polyamine backbone on Spermidine transport inhibition. Covassin, L. et al Bioorganic & Medicinal Chemistry Letters 2003, 13, 3267-3271; b) 2,2'-Dithiobis(N-ethyl-spermine-5-carboxamide) is a high affinity, membrane-impermeant Antagonist of the mammalian Polyamine transport system. Hubert, M. et al Journal of Biological Chemistry, 1996, 271, 27556-27563. c) Covassin. L.; Desjardins, M.; Charest-Gaudreault, R.; Audette, M.; Bonneau, M. J.; Poulin, R. Synthesis of spermidine and norspermidine dimers as high affinity polyamine transport inhibitors. Bioorg. Med. Chem. Lett. 1999, 9, 1709-1714.

5) Aziz paper on polySPM: A novel polymeric spermine conjugate inhibits Polyamine transport in Pulmonary Artery Smooth Muscle cells. Aziz, S. M. et al. JPET 1995, 274, 181-186.

The Burns materials may be degraded via the action of amine oxidases. The inventors' designs address this issue by providing, in one embodiment, multimeric polyamine scaffolds that are N-methylated to protect against amine oxidases. The Poulin PAT inhibitors did not contain the optimal substitution pattern on the polyamine (they were internally substituted vs ours which are terminally substituted). In addition, the inventors' design of new molecules have built-in solutions to the common problems of polyamine drugs, namely metabolic stability and ability to target the polyamine transporter itself with high affinity. For example, N-methylation of the terminal polyamine chain was shown to block the action of amine oxidases a common problem with polyamine drug candidates and yet still retain selectivity for targeting the polyamine transporter. (Designing the Polyamine Pharmacophore: Influence of N-substituents on the transport behavior of polyamine conjugates, Navneet Kaur[†], Jean-Guy Delcros[§], Jennifer Archer[†] Nathan Z. Weagraff[†], Bénédicte Martin[§] and Otto Phanstiel IV[†]* J. Med. Chem. 2008, 51, 2551-2560). N1-substitution was found to optimize delivery to the PAT. The inventors have achieved optimized PAT inhibitors which are metabolically stable and target the PAT with tailored affinities.

Another advantage is the cost of manufacture. The inventors' synthesis is modular and convergent, while others are linear.

Uses.

Figure 10:
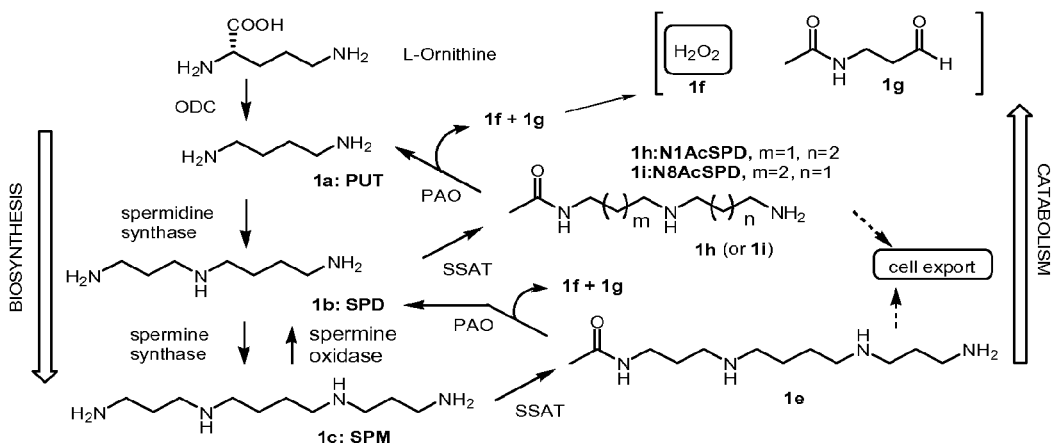
FIG. 10 relates to a diagram of polyamine metabolism pathways.
Figure 11:
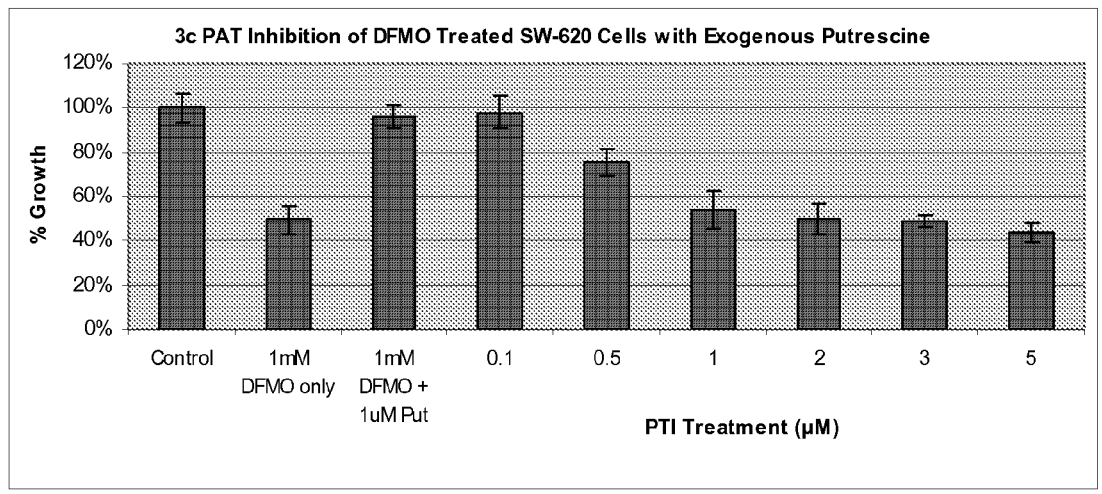
FIG. 11 The above results indicate that compound 3c is an effective treatment starting at 1 µM against L3.6pl metastatic pancreatic cancer when competing with 1 µM of putrescine. The MTD of 3c in this cell line is 5 µM. All treatments (DFMO, putrescine, and 3c) were dosed simultaneously and for a duration of 72 hours.
Figure 12:
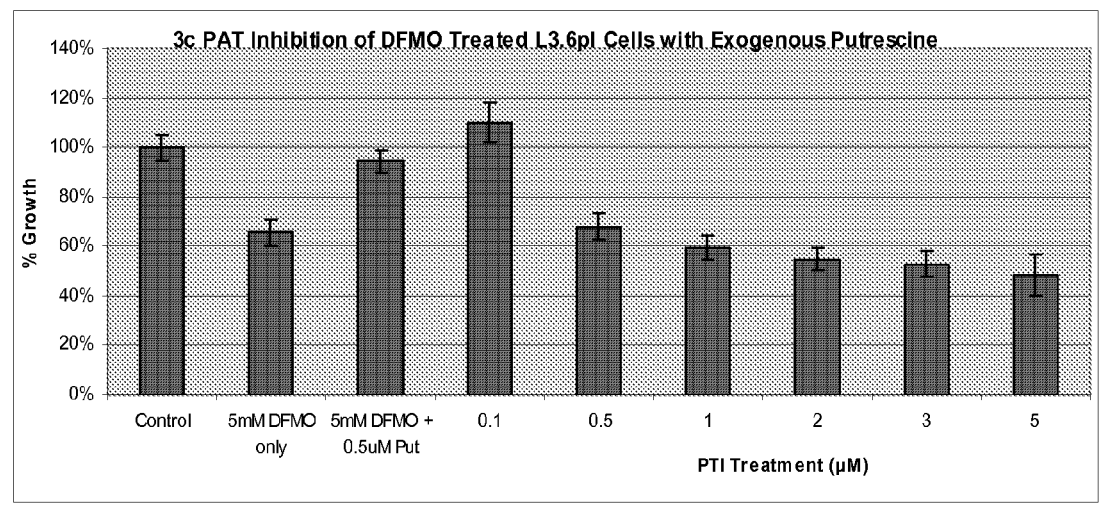
FIG. 12 The above results indicate that compound 3c is an effective treatment starting at 0.5 µM against L3.6pl metastatic pancreatic cancer when competing with 0.5 µM of putrescine. The MTD of 3c in this cell line is 5 µM. All treatments (DFMO, putrescine, and 3c) were dosed simultaneously and for a duration of 48 hours.
Figure 13:
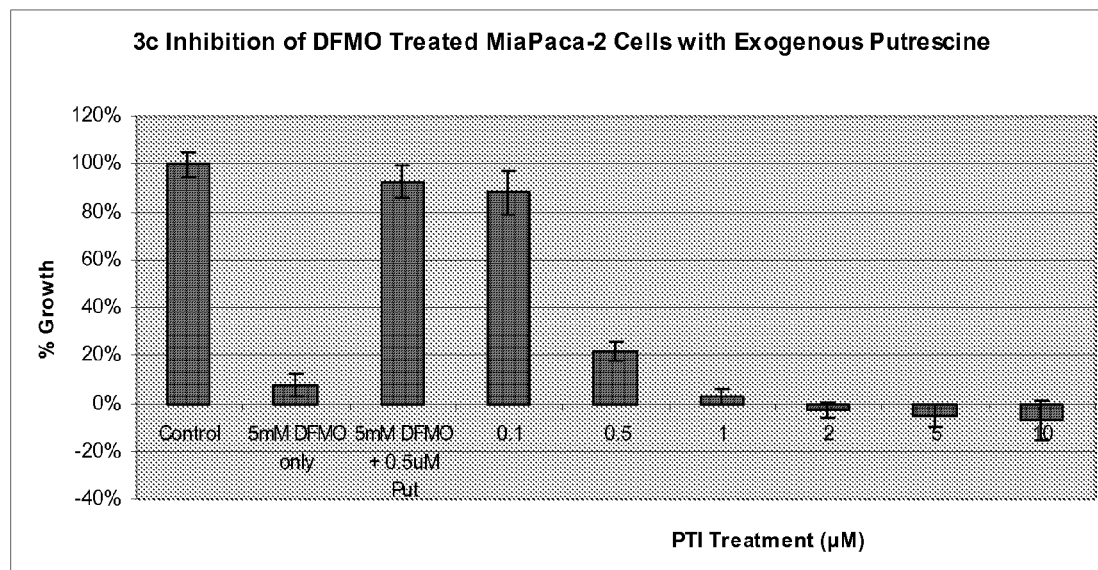
FIG. 13 The above results indicate that compound 3c is an effective treatment starting at 1 µM against MiaPaca-2 pancreatic cancer (primary tumor—not metastatic) when competing with 0.5 µM of putrescine. An incomplete but effective treatment was also observed at 0.5 µM of 3c. The MTD under DFMO treatment of 3c in this cell line is 1 µM and as such the therapy became toxic at 2 µM. If the therapy is not toxic to normal cells, then this therapy is also valid for concentrations above 1 µM. All treatments (DFMO, putrescine, and 3c) were dosed simultaneously and for a duration of 96 hours. DFMO reduction in cell growth was time dependent and gave greater growth reduction at 96 hours than at 48 and 72 hours respectively.

The inhibitors can be used to block uptake of polyamines into cancer cells and thereby regulate their growth. In addition, they can be used in combination with other drugs which block specific enzymes associated with polyamine metabolism. For example, as shown in FIG. 10, DFMO blocks ODC activity which limits the putrescine (PUT, 1a) content of the cell. In response the cells import putrescine from outside the cell via the PAT. Blockade of PAT would limit the ability of these cells to escape the enzyme inhibitors effects and would eventually cause the cell to undergo apoptosis and die due to polyamine depletion and or the generation of reactive oxygen species like hydrogen peroxide (compd 1f in FIG. 10) which is the result of polyamine oxidase (PAO) enzyme activity. Note PAO is responsible for converting N-acetylspermidine and N-acetylspermine to putrescine (PUT) and spermidine (SPD), respectively. The reactive oxygen species hydrogen peroxide could cause cell damage and apoptosis.

a) Chaturvedi, R.; Cheng, Y.; Asim, M.; Bussière, F. I.; Xu, H.; Gobert, A. P.; Hacker, A.; Casero, Jr., R. A.; Wilson, K. T. Induction of Polyamine Oxidase 1 by *Helicobacter pylori* Causes Macrophage Apoptosis by Hydrogen Peroxide Release and Mitochondrial Membrane Depolarization. *J. Biol. Chem.* 2004, 279, 40161-40173.

b) Lasbury, M. E.; Merali, S.; Durant, P. J.; Tschang, D.; Ray, C. A.; Lee, C-H. Polyamine-mediated Apoptosis of Alveolar Macrophages during *Pneumocystis* Pneumonia. *J. Biol. Chem.* 2007, 282, 11009-11020.

Colon cancer cells (RKO, SW620 and SW480) have been shown to be sensitive to this strategy. As shown in the earlier FIGS. 2, 6, and 7, a combination therapy of DFMO and a PAT inhibitor have been shown to have synergistic effects. The PAT inhibitor blocks the native polyamine from rescuing the cells from the DFMO inhibitor. Prolonged blockade of PAT has been shown to increase the toxicity of the DFMO treatment.

Figure 3:
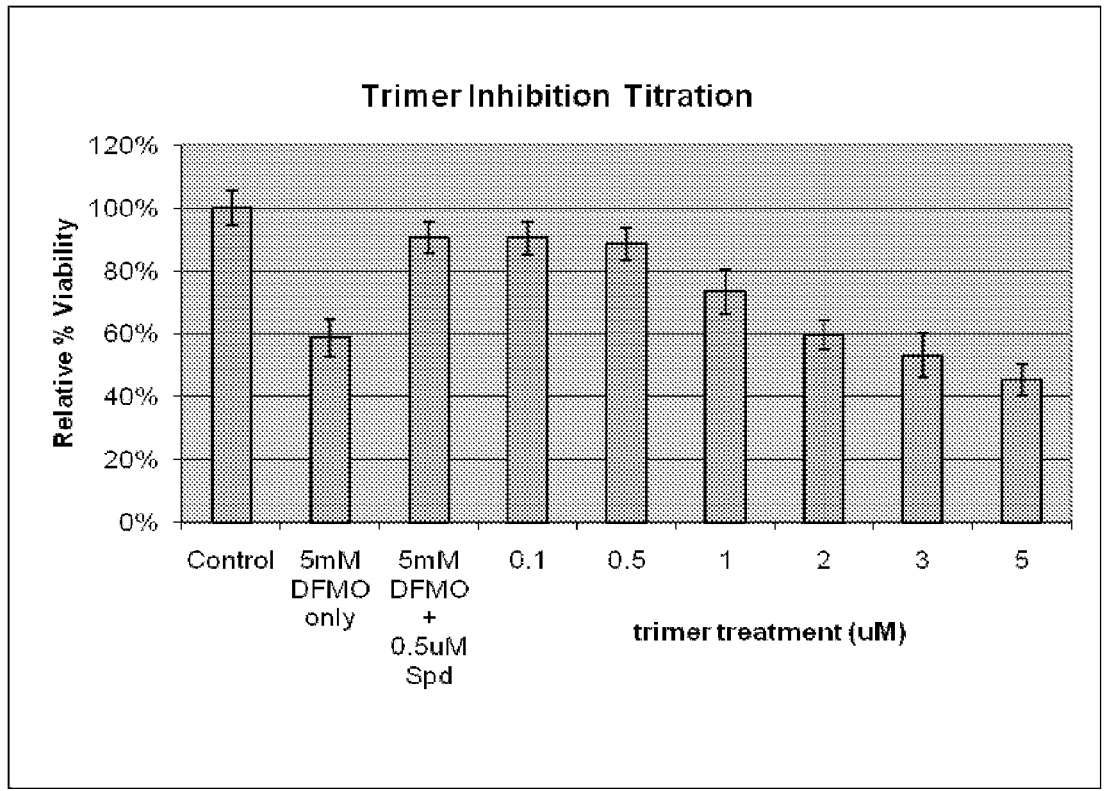
FIG. 3 is a chart showing the block of spermidine rescue by trimer in a does dependent fashion in L3.6pl cells.

In another embodiment, metastatic human pancreatic cancer cells (L3.6pl) were shown to be sensitive to the same strategy. As shown in FIG. 3, a combination therapy of DFMO and a PAT inhibitor was also shown to have synergistic effects in the metastatic human cancer cells. The PAT inhibitor blocked spermidine from rescuing the cells from the DFMO inhibitor. In another embodiment, the methods described herein may be used in the treatment of inflammatory bowel diseases based upon our observations of high polyamine content in these tissues and the observation by others that ODC activity is low and SSAT activity is high, all hallmarks of high intracellular content instigated by high polyamine transport activity. It is believed that PAT inhibitors will block this import process and facilitate ameliorization of the patient's condition by modulating the immune response (increased macrophage activity). Obayashi, M.; Matsui-Yuasa, I.; Matsumoto, T. et al. Polyamine metabolism in colonic mucosa from patients with ulcerative colitis. *Am. J. Gastroenterol.* 1992, 87, 736-740.

Weiss, T. S.; Herfarth, H.; Obermeier, F. et al. Intracellular Polyamine Levels of Intestinal Epithelial Cells in Inflammatory Bowel Disease. *Inflamm. Bowel Dis.* 2004, 10, 529-535.

Ha, H. C.; Woster, P. M.; Yager, J. D. et al. The role of polyamine catabolism in polyamine analogue-induced programmed cell death. *Proc Natl Acad Sci USA.* 1997, 94, 11557-11562.

Deficiency in the Prior Art.

The prior art did not understand the optimal messages required to target the PAT. The extensive structure activity studies revealed herein have unveiled the key structures needed to target the PAT. For example, Poulin used branched polyamines based upon Porter's early observation that N4-substituted SPD was imported into cells. This lone observation propagated the myth that internally substituted polyamines were the way to go for inhibitor design. Since then the inventors have shown that linear polyamines are better than branched polyamines for targeting the transporter. Other investigators have been concerned with but have not addressed the metabolism issues of their designs. The inventors have solved one of them via chemical modifications (N-methylation of the amine terminus to avoid amine oxidase activity). While others have made bis-alkylpolyamines, those disclosed herein have been optimized for targeting the polyamine transporter.

Some adducts will make putrescine-specific transport inhibitors like 5c. These will have utility for use in combination therapy of a polyamine metabolism enzyme inhibitor like DFMO and use the PAT inhibitor to provide synergistic action by blocking the import of polyamines (an import event which would rescue the cancer cell). While many cancers could be treated this way based upon our results and those of others, breast, prostate and colon may be the most beneficial. In addition, PAT inhibition may benefit patients infected with *Pneumocystis* pneumonia.

Figure 4:
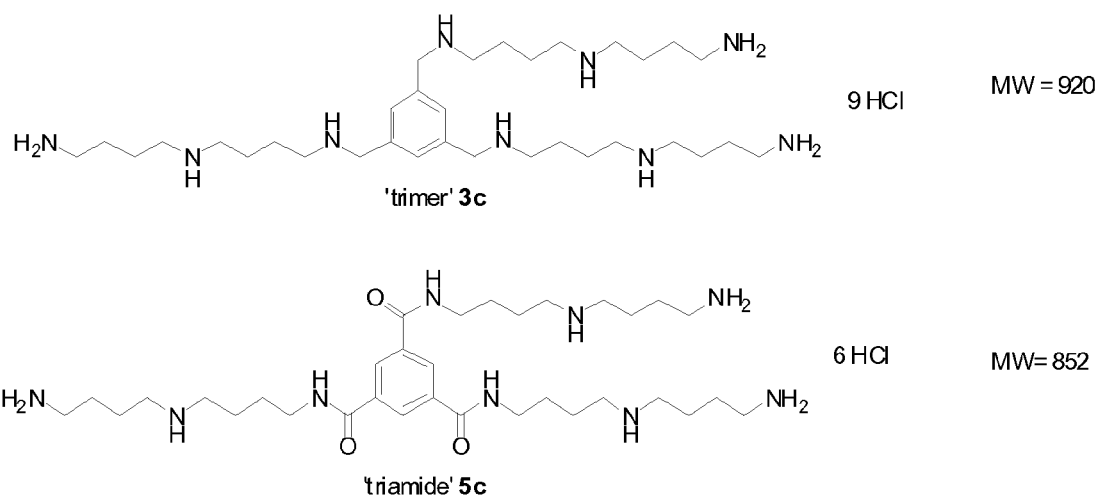
FIG. 4 relates to a diagram showing the structure of specific trimer and triamide embodiments.

Other references for Phanstiel on polyamines and their transport into cells as well as ref 2 which show the construction of the selectively protected polyamines needed in the modular synthesis (FIG. 4).

1. a) Phanstiel I V, O.; Price, H. L.; Wang, L.; Juusola, J.; Kline, M.; Shah, S. M. The Effect of Polyamine Homologation on the Transport and Cytotoxicity Properties of Polyamine-(DNA-Intercalator) Conjugates. *J. Org. Chem.* 2000, 65, 5590-5599. b) Wang, L.; Price, H. L.; Juusola, J.; Kline, M.; Phanstiel, IV, O. The Influence of Polyamine Architecture on the Transport and Topoisomerase II Inhibitory Properties of Polyamine DNA-Intercalator Conjugates, *J. Med. Chem.* 2001, 44, 3682-3691. c) Wang, C.; Delcros, J-G.; Biggerstaff, J.; Phanstiel IV, O. Synthesis and Biological Evaluation of $N^1$-(anthracen-9-ylmethyl) triamines as Molecular Recognition Elements for the Polyamine Transporter, *J. Med. Chem.* 2003, 46, 2663-2671. d) Wang, C.; Delcros, J-G.; Biggerstaff, J.; Phanstiel IV, O. Molecular Requirements for Targeting the Polyamine Transport System: Synthesis and Biological Evaluation of Polyamine-Anthracene Conjugates, *J. Med. Chem.* 2003, 46, 2672-2682. e) Wang, C.; Delcros, J-G.; Cannon, L.; Konate, F.; Carias, H.; Biggerstaff, J.; Gardner, R. A.; Phanstiel IV, O. Defining the Molecular Requirements for the Selective Delivery of Polyamine-Conjugates into Cells Containing Active Polyamine Transporters, J. Med. Chem. 2003, 46, 5129-5138; f) Gardner, R. A.; Delcros, J-G; Konate, F.; Breitbeil III, F.; Martin, B.; Sigman, M.; Phanstiel IV, O. "$N^1$-Substituent effects in the selective delivery of polyamine-conjugates into cells containing active polyamine transporters," *J. Med. Chem.* 2004, 47, 6055-6069; g) Kaur, N.; Delcros, J-G.; Imran, J.; Khaled, A.; Chehtane, M.; Tschammer, N.; Martin, B. and Phanstiel IV, O. A Comparison of Chloroambucil- and Xylene-containing Polyamines Leads to Improved Ligands for Accessing the Polyamine Transport System. *J. Med. Chem.* 2008, 51, 1393-1401. h) Kaur, N.; Delcros, J-G.; Archer, J.; Weagraff, N. Z.; Martin, B.; Phanstiel IV, O. Designing the Polyamine Pharmacophore: Influence of N-substituents on the transport behavior of polyamine conjugates, *J. Med. Chem.* 2008, 51, 2551-2560.

2. This paper describes how the selectively protected polyamine piece is made in the modular synthetic scheme in FIG. 4 (see bracketed polyamines in bottom of FIG. 4), Gardner, R. A.; Kinkade, R.; Wang, C.; Phanstiel IV, O. Total Synthesis of Petrobactin and Its Homologues as Potential Growth Stimuli for *Marinobacter hydrocarbonoclasticus*, an oil-degrading bacteria. *J. Org. Chem.* 2004, 69, 3530-3537.

The teachings of all cited references are incorporated in their entirety to the extent they are not inconsistent with the teachings herein. U.S. Patent Pubs 20090069441, 20090155265, and 20070213397 are cited for background information, as well as teachings on pharmaceutical compositions, formulations, dosages and modes of administration that can be applied to the compounds and compound combinations described herein.

The invention claimed is:

1. A compound 3d, 3e, 3f, 4a, 4b, 4c, 4d, 5a, 5b, 5c, 5d, 5e, 5f, 6a, 6b, 6c, 6d, 7a, 7b, 7c, 7d, 8a, 8b, 8c, 8d, 8e, 8f, 9a, 9b, 9c, 9d, 10a, 10b, 10c or 10d, according to the formulas provided below,

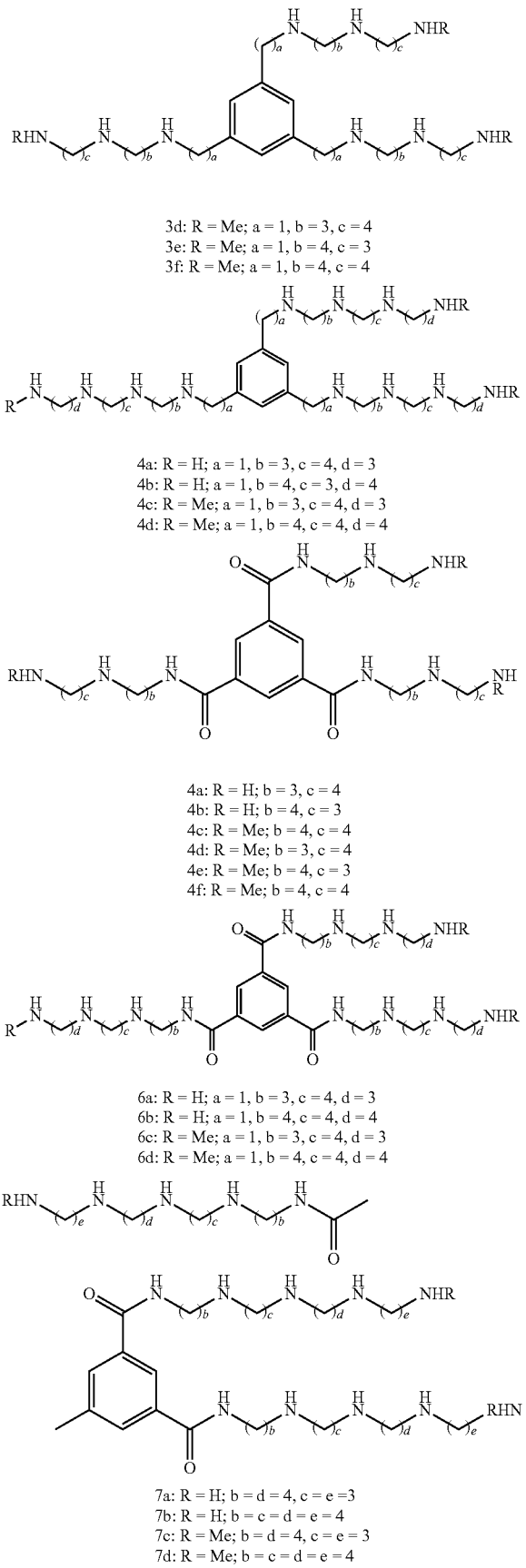

-continued

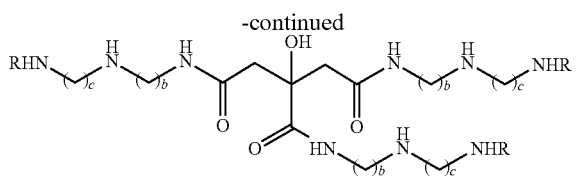

8a: R = H; b = 3, c = 4
8b: R = H; b = 4, c = 3
8c: R = H; b = 4, c = 4
8d: R = Me; b = 3, c = 4
8e: R = Me; b = 4, c = 3
8f: R = Me; b = 4, c = 4

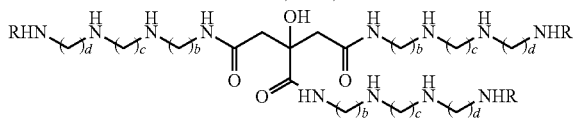

9a: R = H; b = 3, c = 4, d = 3
9b: R = H; b = 4, c = 4, d = 4
9a: R = Me; b = 3, c = 4, d = 3
9b: R = Me; b = 4, c = 4, d = 4

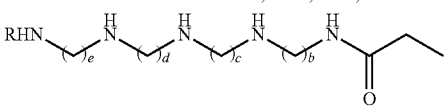

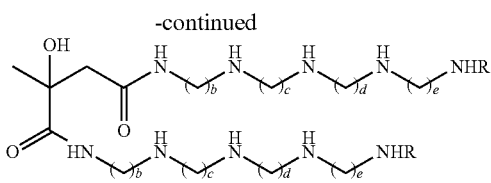

10a: R = H; b = 4, c = 3, d = 4, e = 3
10b: R = H; b = 4, c = 3, d = 4, e = 4
10c: R = Me; b = 4, c = 3, d = 4, e = 3
10d: R = Me; b = 4, c = 4, d = 4, e = 4 or a pharmaceutically acceptable salt thereof.

2. A pharmaceutical composition comprising at least one compound of claim 1 or a pharmaceutically acceptable salt thereof and a pharmaceutically acceptable carrier.

3. A pharmaceutical composition comprising at least one compound of claim 1 or a pharmaceutically acceptable salt thereof, DFMO, and a pharmaceutically acceptable carrier.

4. The composition of claim 3, further comprising a NSAID.

* * * * *